United States Patent
Textor et al.

(10) Patent No.: US 8,568,872 B2
(45) Date of Patent: Oct. 29, 2013

(54) CATECHOL FUNCTIONALIZED POLYMERS AND METHOD FOR PREPARING THEM

(75) Inventors: Marcus Textor, Zurich (CH); Stefan Zürcher, Zurich (CH); Karl Gademann, Volketswil (CH); Samuele Tosatti, Zurich (CH)

(73) Assignee: Eth Zurich, Zurich (CH)

( * ) Notice: Subject to any disclaimer, the term of this patent is extended or adjusted under 35 U.S.C. 154(b) by 1226 days.

(21) Appl. No.: 12/064,564

(22) PCT Filed: Aug. 24, 2005

(86) PCT No.: PCT/CH2005/000494
§ 371 (c)(1), (2), (4) Date: Oct. 22, 2008

(87) PCT Pub. No.: WO2007/022645
PCT Pub. Date: Mar. 1, 2007

(65) Prior Publication Data
US 2009/0093610 A1 Apr. 9, 2009

(51) Int. Cl.
*B32B 3/00* (2006.01)

(52) U.S. Cl.
USPC ........ 428/336; 428/413; 428/447; 428/474.4; 428/500; 528/363

(58) Field of Classification Search
USPC ................ 528/363; 428/447, 474.4, 500, 336
See application file for complete search history.

(56) References Cited

U.S. PATENT DOCUMENTS

| | | | |
|---|---|---|---|
| 4,585,585 A | 4/1986 | Waite | |
| 7,858,679 B2 * | 12/2010 | Messersmith et al. | 524/17 |
| 2003/0044353 A1 * | 3/2003 | Weissleder et al. | 424/9.6 |

FOREIGN PATENT DOCUMENTS

| | | |
|---|---|---|
| JP | 2003-137925 A | 5/2003 |
| WO | WO 03/008376 A2 | 1/2003 |

OTHER PUBLICATIONS

Bethuel et al Synthesis and evaluation of the bis-nor-anachelin chromophore as potential cyanobacterial ligand, J. Org. chem., 2005,70,6258-6264, published on Web Jul. 9, 2005.*
Topchiyeva, I.N., "Synthesis of Biologically Active Polyethylene Glycol Derivatives. A Review", *Polymer Science U.S.S.R.*, vol. 32, No. 5, pp. 833-851, 1990.

* cited by examiner

*Primary Examiner* — Gregory Listvoyb
(74) *Attorney, Agent, or Firm* — Alston & Bird LLP (57) ABSTRACT

Described are compounds that are capable of forming adlayers, the compounds comprising at least one headgroup A, an optional linker B, a polymer C, a terminal group D and an optional crosslinking group R, wherein the headgroup A is a compound of the following formula $$X-Z^3-Z^2=Z^1-(CH_2)_n-(CH_2)_m-Y$$
$$X-Z^4=Z^5-Z^6-L^1 \quad L^2$$

wherein
X is independently selected from an acidic group,
Y is a group derived from a convenient coupling group,
$Z^1$, $Z^3$, and $Z^4$ are C or $N^+$
$Z^2$, $Z^5$ and $Z^6$ are C-$L^1$ or $N^+$-L, wherein
$L^1$ is H or an electron withdrawing group,
L is $C_1$-$C_6$ alkyl, in particular $C_1$-$C_4$ alkyl
$L^2$ and $L^3$ are independently selected from H or $C_1$-$C_6$ alkyl, or $L^2$ may form together with $L^1$ or L of $Z^6$ a heterocycle, in particular a positively charged heterocycle,
n is 0, or 1, or 2, or 3,
m is 0 or 1.

24 Claims, 3 Drawing Sheets

CATECHOL FUNCTIONALIZED POLYMERS AND METHOD FOR PREPARING THEM

TECHNICAL FIELD

The present invention concerns tools useful for surface medications, in particular tools that allow the formation of stable covalent linkage between adsorbate and surface which results in an increased stability of the formed adlayer.

BACKGROUND ART

Highly controlled physicochemical surface properties are key factors in the development and optimization of devices for different fields, ranging from bio-materials to packaging to automotive applications. A possible way of tailoring the surface chemistry without influencing other surface parameters, such as roughness and optical properties, is to use very thin films, in particular monomolecular adlayers. The general functionality of these molecular systems is three-fold: a binding sequence for the immobilization on the surface, a spacer that often contributes to the functional properties of the surface (stability, diffusion barrier, protein resistance) and a chemical group that presents a particular (bio-)functional moiety. Different combinations of amphiphiles/substrates have been developed and successfully applied in the past years, e.g. alkanethiols on gold or silver,[1, 2] silanes on a variety of substrates,[3-8] alkane phosph(on)ates on metal oxides[9-13] or Pluronics on hydrophobic substrates.[14]

In terms of surface functionalization for biomedical applications, poly(ethylene glycol) has been widely investigated thanks to its non-fouling, protein-resistant properties.[15] Graft co-polymers have been extensively investigated in recent years at the Laboratory for Surface Science and Technology (LSST) of the Swiss Federal Institute of Technology Zurich and today, PEG-graft polyelectrolytes such as poly(L-Lysine)-grafted-poly(ethylene glycol) (PLL-g-PEG) adlayers have become a standard tool for surface modifications of charged substrates. The design of this system is based on a positively charged backbone (PLL, pKa=10.5) and a brush of PEG side chains. Once adsorbed, the backbone forms a stable electrostatic bond to the negatively charged metal-oxide substrate, while the side chains form a dense, closely packed, protein-resistant adlayer towards the biological environment. The possibility of varying the PEG density by changing the ratio between PEG side chains and Lys units,[15] as well as the possibility of adding bio-functionally active moieties such as small proteins[16] or short peptide sequences at the PEG-omega position,[17] makes this systems highly versatile for the development of novel biosensors and biomaterial surfaces.

However, this and the other assembly systems, have limitations in terms of substrate choice, as well as binding strength. Hitherto, only one system has been proven to be able to adsorb and form a stable, nearly covalent bond to almost all types of surfaces (metals,[18, 19] stainless steel,[20] metal oxide or ceramics[21, 22] and polymers[23-28]). This system is based on a non-proteinogenic amino acid: 3,4-dihydroxyphenylalanine (DOPA). Indeed, marine mussels, for example, are known to secrete a number of unique proteins that mediate adhesion to the variety of underwater substrates on which they reside.[29] These so-called mussel-adhesive proteins contain an unusually high concentration of 3,4-dihydroxyphenylalanine (DOPA), which is believed to impart the strong adhesion characteristic of these proteins.[19, 29, 30] Furthermore, Messersmith and coworkers have exploited these adhesive characteristics by coupling DOPA-containing peptides to PEG, and have recently demonstrated that these molecules are capable of modifying metals, metal oxides, semiconductor and polymer surfaces, rendering them resistant to cell adhesion and spreading.[19, 31, 32] The DOPA adhesion mechanism is proposed to function either through chelation of surface bound metal centers or via oxidative crosslinking of DOPA.[20, 33, 34]

In WO 03/008376 it has already been proposed to either couple DOPA to a polymer via an urethane bond or via an ester or an amide bond. In case of attachment via a urethane bond, the carboxylic group can be trans-formed into an ester group.

DOPA analogs are also found in other organisms, such as cyanobacteria. These organisms have faced the challenge of iron acquisition for over 2.5 billion years, and have met this task by developing sophisticated strategies. A key substance is the growth factor anachelin[35, 36] which was evolutionary optimized for binding to Fe(III). This molecule contains a chromophore that is biosynthetically derived from DOPA and contains a positive charge.

Although DOPA including polymers have been found to result in adlayers sufficiently stable for several applications, there is still a need for molecules that are more generally applicable and/or more stable in solution and/or form more stable adlayers.

DISCLOSURE OF THE INVENTION

Hence, it is a general object of the invention to provide an anchoring molecule and/or a polymer comprising such anchoring molecule (also referred to as foot).

It is also an object of the present invention to provide a method for the preparation of such foot and/or polymer, in particular for zwitterionic oxidation stable novel catechol equivalent molecules with the capability of binding on different surfaces such as metals and/or metal oxides and/or polymers, in particular such molecules that form an adlayer able to change the surface properties of such substrates.

It is another object of the present invention to provide a method to chemically functionalize different compounds by using a single or multiple catechol equivalent molecule in order to obtain a novel molecule capable to adsorb on surfaces and such surface modified material.

It is yet another object of the present invention to provide a method of increasing the adsorption kinetic and final stability of the self assembled monolayers.

It is still a further object of the present invention to provide a method to increase the stability of the adlayers, particularly their stability in aqueous media such as buffer solution, serum or blood plasma.

Now, in order to implement these and still further objects of the invention, which will become more readily apparent as the description proceeds, in one aspect, the stable adlayer forming molecule of the present invention is manifested by the features that it has one of the general formulas (A) to (C) below:

wherein A designates at least one headgroup A, B designates an optionally present linker B, C designates a polymer C, D designates an optionally present terminus D and R designates an optionally present crosslinker R, and wherein the headgroup A is a compound of the following formula wherein X is independently from each other selected from an acidic group, such as OH, SH, phosphate, in particular cyclic phosphate, wherein the two X form a heterocycle of type phosphonate, and $N^+R_2H$, wherein the R preferably are independently from each other selected from H or $C_1$-$C_6$ alkyl, in particular $C_1$-$C_4$ alkyl, and preferably both X are OH, Y is a group derived from a convenient coupling group, in particular $NL^3$, or $N^+(L^3)_2$, $Z^1$, $Z^3$, and $Z^4$ are C or $N^+$ $Z^2$, $Z^5$ and $Z^6$ are C-$L^1$ or $N^+$-L, wherein $L^1$ is H or an electron withdrawing group, whereby in the case of $L^1=NR^1R^2R^{3+}$, each of $R^1$, $R^2$, $R^3$ may be selected from $C_1$-$C_6$ alkyl or $C_5$ or $C_6$ aryl, in particular from $C_1$-$C_4$ alkyl, especially from methyl, ethyl, n-propyl or iso-propyl, L is $C_1$-$C_6$ alkyl, in particular $C_1$-$C_4$-alkyl,

$L^2$ and $L^3$ are independently selected from H or $C_1$-$C_6$ alkyl, preferably $C_1$-$C_4$ alkyl, or $L^2$ may form together with $L^1$ or L of $Z^6$ a heterocycle, in particular a positively charged heterocycle, n is 0, or 1, or 2, or 3, m is 0 or 1 with the proviso that at most one of $Z^1$ to $Z^6$ is $N^+$ and that in case that $Z^1$ is $N^+$, $L^2$ may additionally be an ester, an amide, or a heterocycle such as oxazole, tetrazole, imidazole etc the optional linker B refers to one of the general formulas I, II, III or IV below where m and n are independently from each other 0, 1, 2, 3, 4, or 5, A refers to the headgroup A described above, and C refers to the polymer C, said polymer C being either of the general formula I or II $$X-Y-Z \quad \text{I}$$

$$Y-(Y)_n-Y-Y \quad \text{II}$$
$$\phantom{Y-(Y)_n-}\overset{|}{X}\phantom{-}\overset{|}{X}$$

wherein

X is a group which can be chemically coupled to either A or the optional linker B, Y is a polymer, or an optionally substituted $(CR^2)_n$-chain with n being at least 3, if a hydrophobic surface is desired preferably at least 6, and R preferably being H or F Z is a functional group suitable for coupling to a terminus D, and the optional terminus D is either an inert group or a reactive group, and the optional crosslinker R is any molecule capable of crosslinking.

In a preferred embodiment, the polymer C is water-soluble.

In the scope of the invention it has been found that catechol equivalent molecules are a useful tool for surface modifications that allow the formation of stable covalent linkage between adsorbate and surface which will increase the stability of the formed adlayer. In the catechol equivalent molecules, the catechol equivalents (feet) can be attached to single functionalized rests (such as a PEG chain) or to already synthesized poly-functionalized polymers thereby making use of the advantages of multi-side attachment.

It has surprisingly been found that catechol equivalents lacking a carboxylic acid, ester or amide group are suitably adsorbed to many different surfaces, although the interaction of the carboxylate, that in case of DOPA has been assumed to be responsible for fast initial adsorption to presumably positively charged surfaces, is not present.

One possible candidate compound lacking the carboxylate function is e.g. dopamine. In the case of urethane bond coupling of e.g. polyethylene glycol (PEG) to dopamine only negligible or no interaction of the formed urethane bond with the surface is expected, and thus said initial adlayer formation is in a broad range surface independent. A low $pK_a$ is assumed to favor the formation of covalent bonds and thus to influence the kinetics of at least the second step, the stability providing step.

In the scope of the present invention it has also been found that further amendments to the catechol equivalents enhance the adsorption kinetics and/or the adlayer stability and/or the oxidation stability of the catechol equivalent, the catechol equivalent molecule, or the catechol equivalent comprising adlayer.

It has been found that the adsorption kinetics to a broad variety of substrates can be enhanced if an electron withdrawing group is attached to the aromatic ring, in particular a permanent positive charge. If a non-charged electron withdrawing group is attached to the aromatic ring, e.g. a nitro group, it will merely lead to the stabilization of a negative charge on a covalent bond forming group, in particular a deprotonated hydroxy group, or to the lowering of the $pK_a$ of the hydroxy group. If a positively charged group is added, the initial adlayer formation on negatively charged surfaces will be favored. Suitable for the introduction of the preferred permanent charges are in particular quarternary amino groups. Since electron withdrawing groups have the $pK_a$ lowering effect already addressed above, they have the advantage that already at a slightly acidic pH significant deprotonation is found such that already at slightly acidic pH the formation of covalent bonds is furthered. In any case, a lowering of the binding energy to a positively charged leaving group can be assumed to result in an improved behavior upon the formation of a covalent bond between the surface of the substrate and the covalently binding groups of the catechol equivalent.

The $pK_a$ lowering effect of specific substitution as found in Literature is shown in Table 1 below:

TABLE 1

| Compound | $pK_{a1}$ | $pK_{a2}$ |
|---|---|---|
| Ethanol | 15.9 | |
| Methanol | 15.5 | |
| α-D-glucose | 12.5 | |
| Phenol | 10.0 | |
| Catechol | 9.3 | 13.0 |
| DOPA | 10.0 | 12.1 |
| Dopamine | 9.1 | 12.0 |
| Anacat | 7.6 | |

In general, the compounds of the present invention have a $pK_{a1}$ of below 10. In a preferred aspect of the present invention, the compounds have a $pK_{a1}$ of below 9.5, more preferred below 9.0, most preferred below 8.5 and especially preferred below 8.

It is also possible to provide other than hydroxy groups as the groups enabling covalent bond formation, provided that they are sufficiently acidic. Such alternative groups are e.g. SH, phosphates, in particular cyclic phosphates, $N^+R_2H$, wherein R independently from each other is a H or $C_1$-$C_6$-alkyl, in particular $C_1$-$C_4$-alkyl In preferred embodiments, however, the adsorbing compound, i.e. the catechol equivalent, has a permanent charge introduced and/or multi attachment sites, i.e. more than one hydroxy group.

In a further aspect of the present invention it has also been found that the oxidation stability can be improved if the positive charge is incorporated into a ring thereby leading to a group as found in anachelin, said group herein being referred to as anacat.

As already mentioned above, the headgroup A is a compound of the following formula wherein in preferred embodiments X is independently from each other OH, SH, phosphate, in particular cyclic phosphate, $N^+R_2H$, wherein R is independently from each other selected from H or $C_1$-$C_6$ alkyl, preferably from $C_1$-$C_4$ alkyl, and much preferred both X are OH, Y is a group derived from a convenient coupling group, in particular $NL^3$, or $N(L^3)_2$ $Z^1$, $Z^3$, and $Z^4$ are C or $N^+$, $Z^2$, $Z^5$, and $Z^6$ are $C$-$L^1$ or $N^+$-L, wherein $L^1$ is H or an electron withdrawing group, preferably a negative charge stabilizing group, such as $NR^1R^2R^{3+}$, or $NO_2$, or F or $C_xF_y$, in particular $CF_3$ or $C_2F_5$, whereby in the case of $L^1 = NR^1R^2R^{3+}$, each of $R^1$, $R^2$, $R^3$ may be selected from C1-C6 alkyl or C5 or C6 aryl, in particular from methyl, ethyl, n-propyl or iso-propyl, L is $C_1$-$C_4$-alkyl, $L^2$ and $L^3$ are independently from each other selected from H or C1-C4 alkyl, or $L^2$ may form together with $R_1$ or $R_2$ or $R_3$ of $L^1$ of $Z^6$, said $L^1$ being a $NR_1R_2R_{3+}$ group, a heterocycle, n is 0, or 1, or 2, or 3, m is 0 or 1, preferably 1 with the proviso that at most one of $Z^1$ to $Z^6$ is $N^+$ and that in case that $Z^1$ is $N^+$, $L^2$ may additionally be an ester, an amide, or a heterocycle such as oxazole, tetrazole, imidazole etc.

The criteria for $Z^1$ to $Z^6$, L and $L^1$ are such that they lead to at least one of the following effects:

lower $pK_a$ value compared to the $pK_{a1}$ of DOPA, the increased hydrophobicity of the molecules between the X groups of the headgroup A, e.g. the catecholic hydroxy groups, and the rest of the molecule stabilizes the surface layer against hydrolysis of the headgroup A-substrate bonds.

In a preferred embodiment, the headgroup A is a group of one of formulas I, or II, or III, or IV below

I

II

-continued

III

IV wherein $R^1$, $R^2$, $L^2$, $L^3$ and n are as defined above, wherein in IV, $L^2$ may also be an ester or amide, but not $CO_2H$ and wherein the deprotonated group indicates the improved deprotonation characteristics of the groups of formula II, III and IV.

Preferred $L^2$ are H or C1-C6-alkyl, much preferred H or C1-C4-alkyl, whereby due to the positive charge also $CONR_2$ and $CO_2R$ are possible, with R independently from each other preferably being H or C1-C6-alkyl, much preferred H or C1-C4-alkyl.

The optional linker B, that—if present—is placed between headgroup A and polymer C is as shown in one of the general formulas I, II, III or IV below

I

II

III

IV where m and n are independently from each other 0, 1, 2, 3, 4, or 5, A refers to the headgroup A described above, and C refers to the polymer C further described below.

The polymer C is derived from polymers of the general formulas I or II below

I

-continued

II wherein

X is a group which can be chemically coupled to either headgroup A or the optional linker B, in general a carboxylate, amine, thiol, hydroxy, sulfone, sulfate, phosphonate, phosphate, etc, in case of a preferred amine group present on the headgroup A (foot molecule) a preferred X is a carboxylate leading to coupling via an amide bond.

Y is a polymer or a $(CR_2)$ chain, preferably a polymer such as polyethylene glycol (PEG), poly-lysine (PL), polymethyloxazoline (PMOXA), polyacrylate, poly(N-vinylpyrrolidone), poly(acrylamide), poly(vinylalcohol), peptoide, peptide, polyester, polysacharide, polyethylene or $(CH_2)_n$ or $(CF_2)_n$, preferably PEG.

Z is a functional group that allows coupling to a terminus D, in particular a group such as OH, COOH, $SO_2H$, $SO_3H$, $NH_2$, SH, etc., preferably OH, $NH_2$, $SO_3H$.

The preferably also present terminus D is either an inert group or a reactive group, in particular an inert group such as an alkyl, aryl, allyl, alkenyl, alkinyl, or polyalkylsilyl group, or a fluorescent marker, a biologically active compound such as a protein, a peptide sequence, a sacharide, or any other biologically active compound, or a reactive group such as a vinylsulfone, maleimide, acrylate, azide or alkine group.

The optionally present crosslinker R is any molecule capable of crosslinking such as catechol, styrene, acrylates, thioles, thiophene, and pyrrole.

In order to improve the stability of the formed adlayer, it may be preferred to have more than one, in general about two or three headgroups A attached to one polymer C. This may be accomplished by using a suitable linker B, resulting in more than one (in general two or three) headgroup A attached to one linker B that again is attached to one polymer C.

Molecules of formulas (A) to (C) are suitable for forming adlayers, or coatings, respectively, on surfaces of a broad variety of substrates such as metals with oxidized/non oxidized surfaces, metal oxides, ceramics, polymers, biological tissues, lipids bilayers, carboxylates such as bone etc., thereby providing the surfaces with desired properties such as protein resistance, e.g anti-fouling properties, hydrophobic or hydrophilic properties, lubrication, especially lubrication in aqueous environment, biomolecule specificity, adhesion/repulsion, cell adhesion etc.

There exist different chains that provide non-fouling properties or that at least lead to reduced fouling. Apart from PEG, also polymethyloxazolin (PMOXA), poly-N-vinylpyrrolidone (PVP), polyacrylamide, etc. are suitable non-fouling chains (see e.g. Whitesides et al.,[1]). It is generally acknowledged that high chain densities of PEG, PMOXA, PVP etc. are essential for non-fouling properties. One of the benefits of the compounds of the present invention is that they allow such high chain densities to be achieved in an easier, more cost-effective way, e.g. at lower temperature, and without requiring multistep surface chemistry leading to different reproducibility.

It is also within the invention to treat the surfaces prior to adlayer formation, e.g. polymer surfaces to remove adventitious contamination, or to increase reactivity of the surface.

The molecules of the present invention are preferably applied from aqueous solutions, in particular aqueous solutions wherein at least 1%, preferably at least 3% much preferred at least 5% of the covalent bond forming groups are present in dissociated, in particular deprotonated form, e.g. by applying the molecules from an aqueous solution with desired pH. Other methods to select the degree of dissociation such as solvent mixtures may also be applied.

Also within the scope of the present invention are catechol equivalent molecules wherein a combination of different headgroups A and/or a combination of different linkers B and/or a combination of different polymers C and/or a combination of different terminus D and/or a combination of different crosslinkers R are used in the molecule formation.

The molecules of the present invention can be produced using coupling reactions well known to the skilled person.

Specific catechol equivalent molecules of the present invention, suitable for forming adlayers are wherein $R^1$ and $R^2$ are as defined above.

In a second aspect, the stable adlayer forming molecule of the present invention is manifested by the features that it has a $pK_{a1}$ of at most 9.9, in general at most 9.5, preferably at most 9, especially at most 8.5, most preferred at most 8, said compound being capable of forming adlayers and having one of the general formulas (A) to (C) below:

wherein A designates at least one headgroup A, B designates an optionally present linker B, C designates a polymer C, D designates an optionally present terminus D and R designates an optionally present crosslinker R, and wherein the headgroup A is a compound of the following formula wherein X is an acidic group, preferably X is independently from each other OH, SH, phosphate, in particular a cyclic phosphate, phosphonate, $NR_2H$, wherein both R independently from each other are selected from H or $C_1$-$C_6$ alkyl, in particular $C_1$-$C_4$ alkyl, and most preferably both X are OH, Y is a group comprising the polymer C and the optionally present linker B, the optionally present terminus D and/or the optionally present crosslinker R, $Z^1$, $Z^3$, and $Z^4$ are C or $N^+$, $Z^2$, $Z^5$ and $Z^6$ are C-$L^1$ or $N^+$-L, whereby $L^1$ is H or an electron withdrawing group, in particular an electron withdrawing group as defined above, and L is a neutral group.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 2 shows XPS of O 1s (FIG. 2A) and C 1s (FIG. 2B) signals for mPEG-L-DOPA, mPEG-Mimosine, mPEG-Dopamine and mPEG-Anacat after adsorption onto TiO2. In the case of mPEG-Dopamine and mPEG-Anacat, a high amount of PEG is visible proofing the adsorption of the mol- ecules, whereas for the other two compounds much less is adsorbed and most of the carbon is due to adventitious carbon from the atmosphere.

MODES FOR CARRYING OUT THE INVENTION

The invention will now be further described by means of specific Examples. The production method for adlayer covered substrates described therein is very generally applicable. Said method comprises treating an optionally pretreated surface with a solution of one or more adlayer forming molecules, in particular a water based solution. The formation of the covalent bonds between substrate and adlayer may be favored by heating, e.g. to about 50° C. Furthermore, increasing the temperature increases also the final PEG density due to a decreased steric volume of the PEG chain upon adsorption (cloud point adsorption). As soon as the adlayer has been formed, the coated substrate can be dried. Specific treating and drying methods that are broadly suitable can be taken from the examples.

Example 1 mPEG Anacat

Anacat (prepared according to Karl Gademann, 2005[37]) (6.8 mg, 22 µmol) was dissolved at 0° C. (ice-bath) in HCl (4 M) and dioxane (0.5 ml). The reaction mixture was stirred for 1.5 h at 0° C., whereas after 30 minutes a yellow-orange precipitate formed, and for 10 minutes at RT under argon (Ar). The solvent was removed under reduced pressure and the resulting off-white powder was dried under high vacuum. The residue was suspended in DMF (1 ml) and $CH_2Cl_2$ (1 ml) and N-methylmorpholine (50 µl) was added. Additional DMF (1 ml) was added and the reaction mixture was stirred for 15 minutes until an orange-yellow solution resulted. Methoxy-PEG-hydroxyacetate-hydroxysuccinidyl ester (mPEG-ASA) (50 mg, ca. 10 µmol) was added in one portion and the orange-yellow solution was stirred at RT under Ar under the exclusion of light for 18 h. The reaction mixture was then filtered, and diluted with 50 ml diethylether. The solution was allowed to stand for 30 minutes at 4° C., after which a white precipitate formed. The precipitate was filtered and washed extensively with diethylether. The product was dried under high vacuum to give 33.2 mg (ca 6.6 µmol, 66%) orange solid.

Example 2 mPEG-Dopamine

Dopamine (1.9 mg, 10 µmol) was dissolved in $CH_2Cl_2$ (0.3 ml) and DMF (0.05 ml) and stirred 10 minutes at RT. Then mPEG-ASA (5.5 mg, 1.1 µmol) was added and the mixture stirred at RT for 3 hours. Then ether (0.5 ml) was added and the reaction mixture stirred at RT for 20 minutes. The suspension was filtered and the filtrate purified by chromatography on Sephadex LH-20 with methanol. The fractions containing product were combined and the solvent evaporated under reduced pressure to give the target compound as white solid.

Example 3

Dopamine/mPEG-Dopamine Co-Polymer

Dopamine hydrochloride (7.4 mg, 0.0194 mmol) and mPEG (5 kDa)-dopamine (100 mg, 0.0194 mmol) were dissolved in 7 mL water. 1 mL of 1N sodium hydroxid solution was added and the mixture was stirred for 17 hours at room temperature. The resulting solution was acidified with 1 mL of 2 N HCl, filtered and dialyzed against ultrapure water. The final solution was lyophilized to give 100 mg poly(mPEG-dopamin/dopamine). The ratios between dopamine and PEG dopamine can be varied. The reaction conditions lead to a ring closure by a nucleophilic attack of the amine/amide which is proofed by the loss of aromatic protons in the $^1$H-NMR spectrum.

Example 4 mPEG-Di-Dopamine

N-Benzyloxycarbonylglutamate (Z-Glu) (0.281 g, 1 mmol) was dissolved in CH$_2$Cl$_2$ (5 ml) and cooled to 0° C. Triethylamine (1.53 ml, 11 mmol), dopamine (0.417 g, 2.2 mmol), butanol (HOBt) (0.297 g, 2.2 mmol) and N,N-Dimethylaminopropyl-ethyl-carbodiimide (EDC) (0.412 g, 2.2 mmol) were added in small portions. The reaction mixture was allowed to warm to RT and stirred for 16 h. The solvent was evaporated and citric acid solution (10%, 3 ml) and acetic acid ethyl ester (EtOAc) (20 ml) were added. The flask was shaken vigorously and the layers separated. The organic layer was dried (MgSO$_4$), filtered, and the solvent evaporated. The residue was taken up in 1 N HCl solution (6 ml) and the aqueous layer was three times extracted with EtOAC (15 ml each). The combined organic layers were dried (MgSO$_4$), filtered, and the solvent evaporated. The residue was dissolved in methanol (5 ml), Pd/C (1 spatula, 10% Pd) was added, and the reaction mixture was stirred under an atmosphere of hydrogen for 3 h at RT. The reaction mixture was filtered over Celite and the solvent evaporated and dried under high vacuum to give an intermediate amine (48.1 mg, 0.1235 mmol, 92%). This intermediate amine (11.1 mg, 28.5 umol) was dissolved in CH$_2$Cl$_2$ (1 ml) and DMF (1 ml). mPEG-ASA (50 mg, ca 10 umol) was added at RT and the reaction mixture was stirred under Ar over night. Diethylether (20 ml) was added to the reaction mixture and a white precipitate formed at 4° C. after 30 minutes. This powder was collected by filtration, dried (high vacuum), and purified by Sephadex (MeOH). The fractions containing product were collected, the solvent removed under reduced pressure, the residue dissolved in H$_2$O and the solution was lyophilized to give target compound (35 mg, ca 6.4 μmol, 64%) as colorless powder.

Example 5 mPEG-Mimosine

Mimosine (10 mg, 0.05 mmol) was dissolved in 5 mL of sodiumborate buffer (50 mM, pH 8.4). mPEG-ASA (252 mg, 0.05 mmol) was added and the resulting mixture was stirred at room temperature for 16 hours. 0.5 mL of HCl (2 N) solution were added. The compound was extracted into chloroform and the combined organic phases were dried with $MgSO_4$. After reducing the solvent to 5 mL, the intermediate product was precipitated by the addition of diethylether. Yield 220 mg mPEG-mimosine as a colorless powder.

Dopamine (1.9 mg, 10 μmol) was dissolved in $CH_2Cl_2$ (0.3 ml) and DMF (0.05 ml) and stirred 10 minutes at RT. Then mPEG-ASA (5.5 mg, 1.1 μmol) was added and the mixture stirred at RT for 3 hours. Then ether (0.5 ml) was added and the reaction mixture stirred at RT for 20 minutes. The suspension was filtered and the filtrate purified by chromatography on Sephadex LH-20 with methanol. The fractions containing product were combined and the solvent evaporated under reduced pressure to give the target compound as white solid.

Example 6

PAAM-g-mPEG-Mimosine 100 mg (0.019 mmol) of mPEG-mimosine and 3.6 mg (0.038 mmol monomers) of poly allylamine (PAAM) hydrochloride (MW 14,000) were dissolved in hepes buffer (10 mmol, pH 7.4). 1-(3-dimethylaminopropyl)-3-ethylcarbodiimide hydrochloride (EDC 3.5 mg, 0.038 mmol) was added. The clear solution was stirred for 16 hours. The whole solution was transferred into a dialysis tube with a MWCO of 3500 and dialized against water for 48 hours. The resulting solution was freeze dried to yield 90 mg polyallylamin-grafted-mPEG-mimosine as a white powder. The ratio between poly allylamine and mPEG-mimosine can be varied.

Example 7

Adsorption onto Surfaces of Cathechol Deviated Compound

Example 7A

Preparation of the Treatment Solution

The molecules were dissolved at a concentration of 0.1-1 mg per mL in a buffer solution of 10 mM 3-morpholinopropanesulfonic acid (MOPS), 0.6M $K_2SO_4$ and 0.6M NaCl at pH=6, the solution being gently shaked. The solution was passed through a 0.22 μm filter (MILLEX-GV, MILLIPORE, Bedford, Mass.).

Sample Treatment

The substrates for the surface modification tests were cleaned upon sonication for 15 min in ultra pure water and then for 15 min in 2-propanol. After drying, they were subjected for 3 min to oxygen-plasma cleaning (Harrick Plasma Cleaner/Sterilizer PDC-32G, Ossining, N.Y., USA). They were then transferred to a glass vessel, to which the aqueous solution of the molecules was then added. After treatment for 4 h at 50° C., the samples were taken out, rinsed with water and dried in a stream of nitrogen. In order to prove the presence of a stable linkage to the substrate, samples were immersed for 48 h in physiological buffer, removed, rinsed with water and dried.

Figure 1:
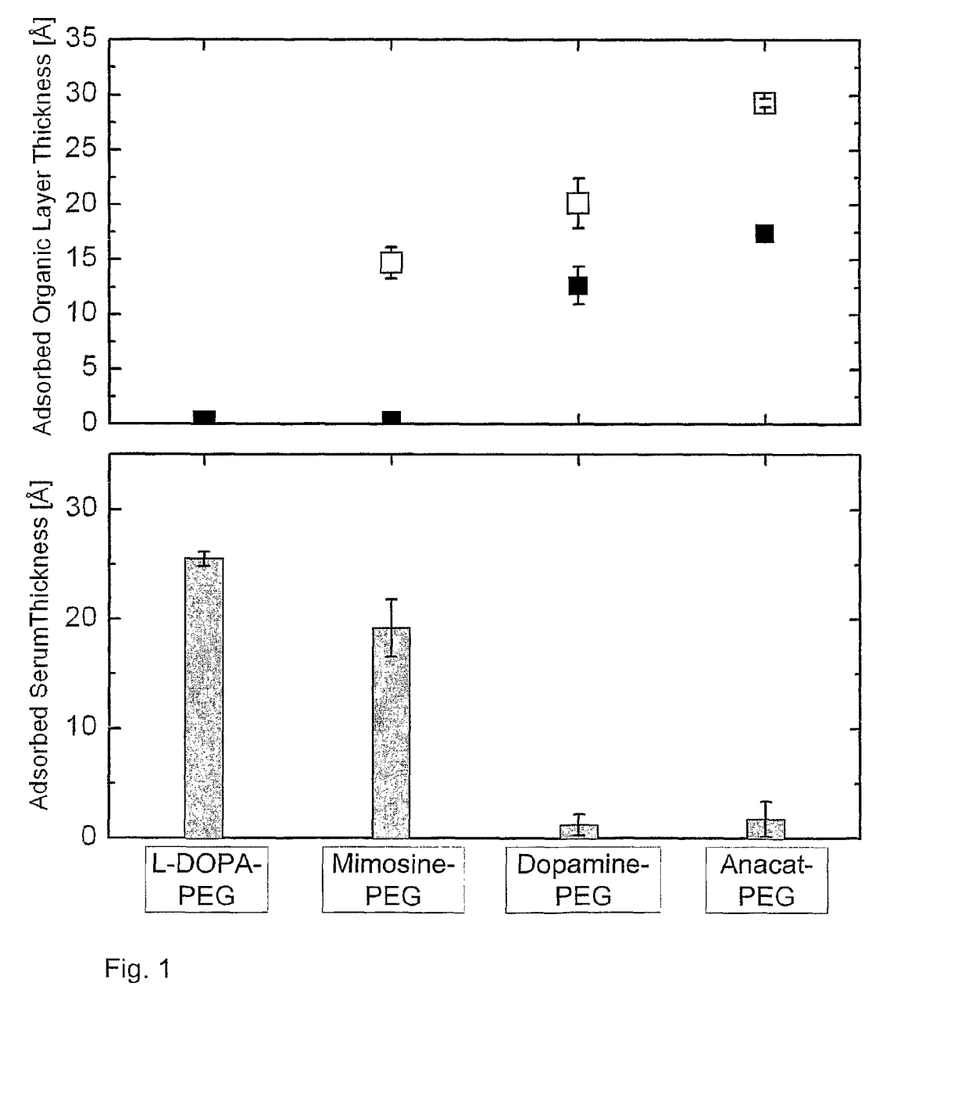
FIG. 1 shows ellipsometry measurements on surfaces modified with different catechol equivalent molecules (mPEG-L-DOPA, mPEG-Mimosine, mPEG-dopamine, mPEG-anacat). In the upper panel the adsorption of the molecules after 4 h in high salt buffer (white square) and after storage in HEPES2 for 48 h (black square) is showed. The lower panel shows serum adsorption on the HEPES 2 stored surfaces.
Figure 2A:
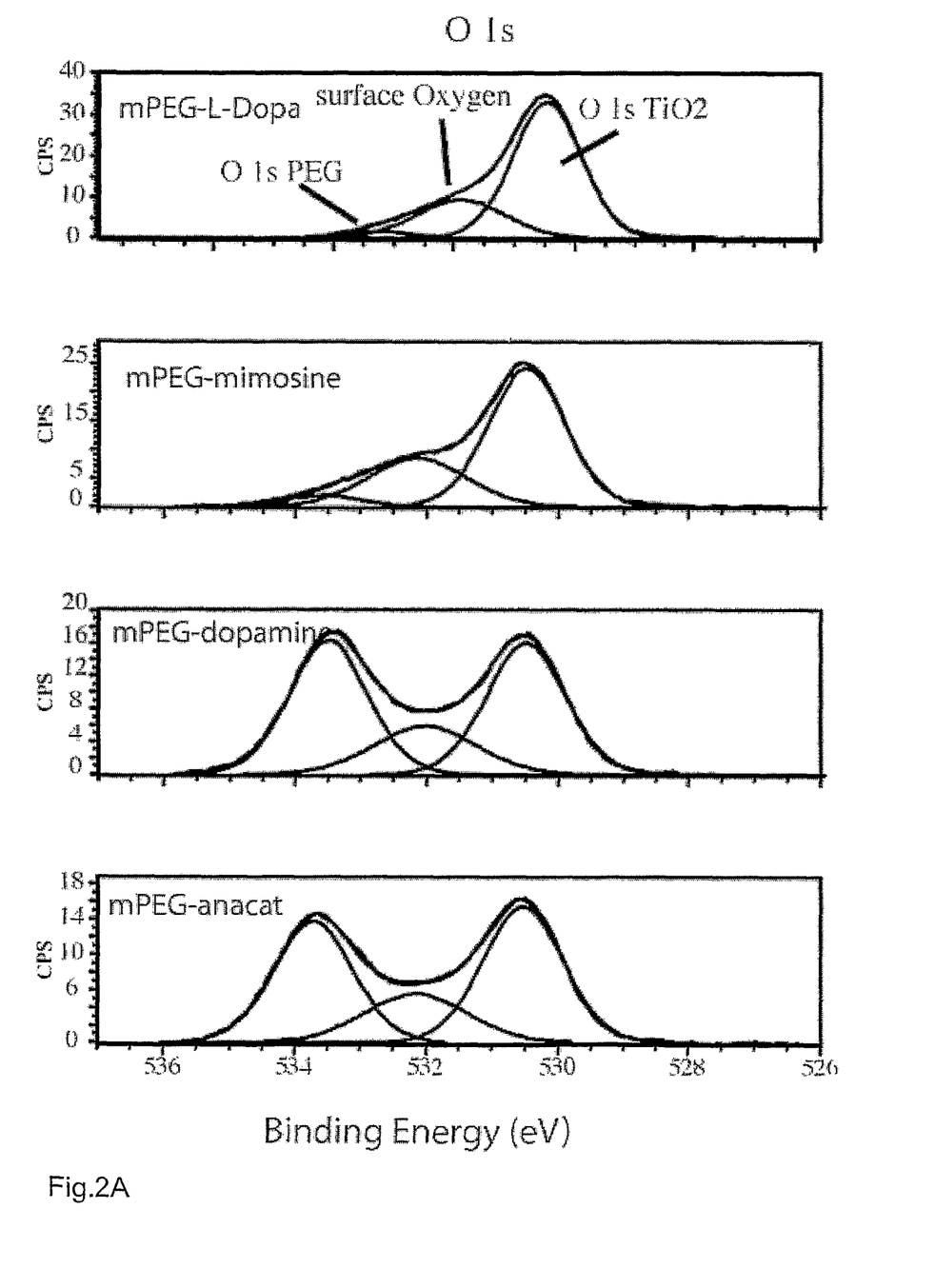
Figure 2B:
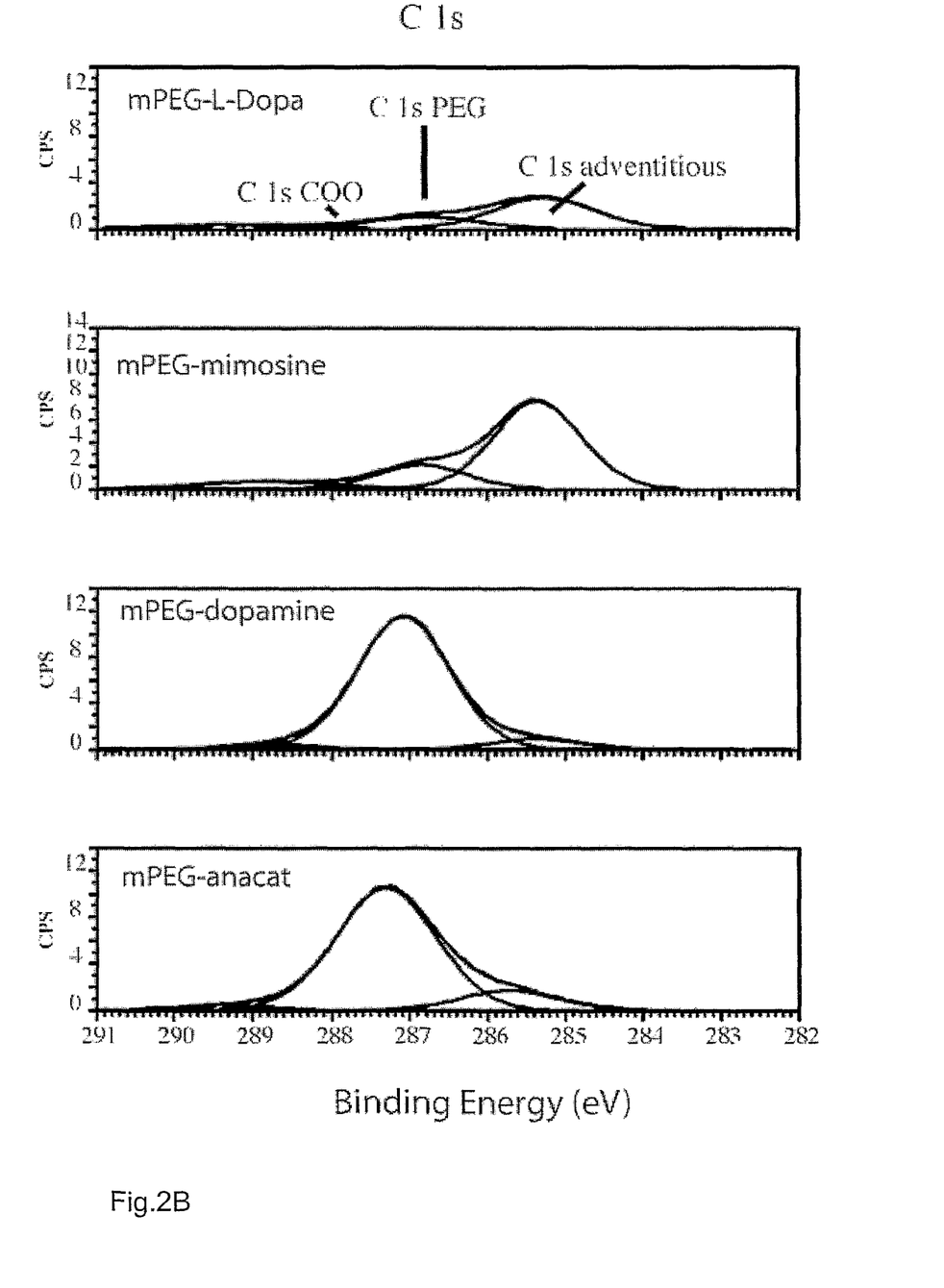

Results a) The Adsorption of the Molecules was Carried Out on Various Substrates The molecules were applied to the following surfaces: $Al_2O_3$, $Cr_2O_3$, $TiO_2$, stainless steel, polystyrene, PVC, Au, $Ta_2O_5$, $Nb_2O_5$, $ZrO_2$, $Fe_2O_3$, $SiO_2$, polyethylene, polyamide, polypropylene (see FIG. 1 for titanium oxide).

b) Adlayer Thickness

The results indicate the deposition of a layer with thickness variable from 1 to 3 nm after exposure to the molecule solution. After immersion in HEPES 2 for 48 h adlayers of samples modified with molecules being neutral or having positive charge, were found to be still present on the surface (see FIG. 1), whereas those formed with molecules carrying a remaining negative carboxylate group were found to be not stable. In particular, molecules with a net positive charge showed improved stability. Even if they also carried a carboxylate group an improved adlayer stability was found.

c) Stability Investigations

Samples immersed in a solution of 0.1 mM HCl for 1 h were shown to remain adherent onto the surface. As comparison, electrostaticly adsorbed molecules such a PLL-g-PEG were shown to be removed after the acid treatment.

d) Determination of Solution Shelf-Life

By use of UV-vis spectroscopy the stability of the polymer solution was determined after 12 h from preparation. Results indicate that L-dopa and dopamine derived molecules start to polymerize and decompose showing a broad adsorption above 400 nm. The molecules having an electron-withdrawing group such as mPEG-anacat or those derived from mimosine did not display a change in their UV-vis spectra indicating a much higher stability. The same result was found by gelpermeation chromatography (GPC) showing an increase in molecular weight for L-dopa and dopamine derived molecules, which proofs, that they are polymerized.

Example 7B

Preparation of the Treatment Solution

The molecules were dissolved at a concentration of 0.1-1 mg in a buffer solution of 10 mM MOPS, 0.6M $K_2SO_4$ at pH=6, the solution being gently shaked. The solution was passed through a 0.22 μm filter (MILLEX-GV, MILLIPORE, Bedford, Mass.). The difference to Example 7A is that there was no additional NaCl added.

Sample Treatment

Samples were treated as in Example 7A.

Result:

The formed layers were slightly less dense than those prepared according to Example 7A.

Example 7C

Preparation of the Treatment Solution

The neutral or positively charged molecules were dissolved at a concentration of 0.1-1 mg in a buffer solutions of 10 mM HEPES and 150 mM NaCl at pH=7.4, the solution being gently shaked. The solution was passed through a 0.22 μm filter (MILLEX-GV, MILLIPORE, Bedford, Mass.).

Sample Treatment

The substrates for the surface modification tests were cleaned upon sonication for 15 min in ultrapure water and then for 15 min in 2-propanol. After drying, they were subjected for 3 min to oxygen-plasma cleaning (Harrick Plasma Cleaner/Sterilizer PDC-32G, Ossining, N.Y., USA). They were then transferred to a glass vessel, to which the aqueous solution of the molecules was then added. After treatment for 1 h at RT a physically adsorbed adlayer was formed. In order to establish a covalent linkage to the surface, the samples were taken and heated to 50° C. for 1 h. As alternative procedure samples can be cured by others methods such as UV-light or white light or other energy delivering methods. Finally the samples were dried in a stream of nitrogen. In order to prove the presence of a stable linkage to the substrate, samples were immersed for 48 h in physiological buffer, removed, rinsed with water and dried.

Example 7D

Preparation of the Treatment Solution

The neutral or positively charged molecules were dissolved at a concentration of 0.1-1 mg in a organic solvent solution (e.g. chloroform), the solution being gently shaked.

Sample Treatment

The substrates for the surface modification tests were cleaned upon sonication for 15 min in ultrapure water and then for 15 min in 2-propanol. After drying, they were subjected for 3 min to oxygen-plasma cleaning (Harrick Plasma Cleaner/Sterilizer PDC-32G, Ossining, N.Y., USA). They were then mounted in a spin-coating device.

The mixture was then spin-cast onto the samples spinning at a speed of 3500 rpm. A uniform uncolored film was normally obtained. After evaporation of the solvent and in order to establish a covalent linkage to the surface, samples were cured at 50° C. to 100° C. for 1 h. As alternative procedure samples can be cured by other methods such as UV-light or white light or other energy delivering methods. Samples were then rinsed with water and dried in a stream of nitrogen. In order to prove the presence of a stable linkage to the substrate, samples were immersed for 48 in physiological buffer, removed, rinsed with water and dried.

While there are shown and described presently preferred embodiments of the invention, it is to be distinctly understood that the invention is not limited thereto but may be otherwise variously embodied and practiced within the scope of the following claims.

REFERENCES

1. Whitesides, G. M.; Jiang, X.; Ostuni, E.; Chapman, R. G.; Grunze, M., SAMS and biofunctional surfaces. The "inert surface" problem. Polymer Preprints (American Chemical Society, Division of Polymer Chemistry) 2004, 45, (1), 90-91.
2. Morgenthaler, S.; Lee, S.; Zürcher, S.; Spencer, N. D., A Simple, Reproducible Approach to the Preparation of Surface-Chemical Gradients. Langmuir 2003, 19, (25), 10459-10462.
3. Moser, A. E.; Eckhardt, C. J., A method for reliable measurement of relative frictional properties of different self-assembled monolayers using frictional force microscopy. Thin Solid Films 2001, 382, (1, 2), 202-213.
4. Masuda, Y.; Seo, W. S.; Koumoto, K., Selective Deposition and Micropatterning of Titanium Dioxide on Self-Assembled Monolayers from a Gas Phase. Langmuir 2001, 17, (16), 4876-4880.
5. Chaki, N. K.; Aslam, M.; Sharma, J.; Vijayamohanan, K., Applications of self-assembled monolayers in materials chemistry. Proceedings—Indian Academy of Sciences, Chemical Sciences 2001, 113, (5-6), 659-670.
6. Iimura, K. i.; Nakajima, Y.; Kato, T., A study on structures and formation mechanisms of self-assembled monolayers of n-alkyltrichlorosilanes using infrared spectroscopy and atomic force microscopy. Thin Solid Films 2000, 379, (1, 2), 230-239.
7. Maoz, R.; Netzer, L.; Gun, J.; Sagiv, J., Self-assembling monolayers in the construction of planned supramolecular structures and as modifiers of surface properties. Journal de Chimie Physique et de Physico-Chimie Biologique 1988, 85, (11-12), 1059-65.
8. Maoz, R.; Yam, R.; Berkovic, G.; Sagiv, J., Third-level self-assembly and beyond: polar hybrid superlattices via postassembly intercalation into noncentrosymmetric multilayer matrices of hydrogen-bonded silanes. Thin Films (San Diego, Calif., United States) 1995, 20, 41-68.
9. Hofer, R.; Textor, M.; Spencer, N. D., Imaging of Surface Heterogeneity by the Microdroplet Condensation Technique. Langmuir 2001, 17, (13), 4123-4125.
10. Tosatti, S.; Michel, R.; Textor, M.; Spencer, N. D., Self-assembled monolayers of dodecyl and hydroxy-dodecyl phosphates on both smooth and rough titanium and titanium oxide surfaces. Langmuir 2002, 18, (9), 3537-3548.
11. Textor, M.; Tosatti, S.; Wieland, M.; Brunette, D. M., Use of molecular assembly techniques for tailoring chemical properties of smooth and rough titanium surfaces. Bio-Implant Interface 2003, 341-366.
12. Danahy, M. P.; Avaltroni, M. J.; Midwood, K. S.; Schwarzbauer, J. E.; Schwartz, J., Self-assembled Monolayers of a,w-Diphosphonic Acids on Ti Enable Complete or Spatially Controlled Surface Derivatization. Langmuir 2004, 20, (13), 5333-5337.
13. Midwood, K. S.; Carolus, M. D.; Danahy, M. P.; Schwarzbauer, J. E.; Schwartz, J., Easy and Efficient Bonding of Biomolecules to an Oxide Surface of Silicon. Langmuir 2004, 20, (13), 5501-5505.
14. Musoke, M.; Luckham, P. F., Interaction forces between polyethylene oxide-polypropylene oxide ABA copolymers adsorbed to hydrophobic surfaces. Journal of Colloid and Interface Science 2004, 277, (1), 62-70.
15. Pasche, S.; De Paul, S. M.; Voeroes, J.; Spencer, N. D.; Textor, M., Poly(L-lysine)-graft-poly(ethylene glycol) assembled monolayers on Niobium Oxide surfaces: a quantitative study of the influence of polymer interfacial architecture on resistance to protein adsorption by ToF-SIMS and in situ OWLSu OWLS. Langmuir 2003, 19, (22), 9216-9225.
16. Huang, N.-P.; Voeroes, J.; De Paul, S. M.; Textor, M.; Spencer, N. D., Biotin-derivatized poly(L-lysine)-g-poly (ethylene glycol): A novel polymeric interface for bioaffinity sensing. Langmuir 2002, 18, (1), 220-230.
17. Tosatti, S.; De Paul, S. M.; Askendal, A.; VandeVondele, S.; Hubbell, J. A.; Tengvall, P.; Textor, M., Peptide functionalized poly(L-lysine)-g-poly(ethylene glycol) on titanium: resistance to protein adsorption in full heparinized human blood plasma. Biomaterials 2003, 24, (27), 4949-4958.
18. Chia, V. K. F.; Soriaga, M. P.; Hubbard, A. T., Kinetics of Oriented Adsorption—Hydroquinone on Platinum. Journal of Physical Chemistry 1987, 91, (1), 78-82.

19. Dalsin, J. L.; Hu, B.-H.; Lee, B. P.; Messersmith, P. B., Mussel Adhesive Protein Mimetic Polymers for the Preparation of Nonfouling Surfaces. Journal of the American Chemical Society 2003, 125, (14), 4253-4258.
20. Hansen, D. C.; Luther, G. W., III; Waite, J. H., The adsorption of the adhesive protein of the blue mussel Mytilus edulis L onto type 340L stainless steel. Journal of Colloid and Interface Science 1994, 168, (1), 206-16.
21. Rodriguez, R.; Blesa, M. A.; Regazzoni, A. E., Surface complexation at the TiO 2 (anatase) aqueous solution interface: Chemisorption of catechol. Journal of Colloid and Interface Science 1996, 177, (1), 122-131.
22. Xu, C.; Xu, K.; Gu, H.; Zheng, R.; Liu, H.; Zhang, X.; Guo, Z.; Xu, B., Dopamine as A Robust Anchor to Immobilize Functional Molecules on the Iron Oxide Shell of Magnetic Nanoparticles. Journal of the American Chemical Society 2004, 126, (32), 9938-9939.
23. Höök, F.; Kasemo, B.; Nylander, T.; Fant, C.; Sott, K.; Elwing, H., Variations in coupled water, viscoelastic properties, and film thickness of a Mefp-1 protein film during adsorption and cross-linking: A quartz crystal microbalance with dissipation monitoring, ellipsometry, and surface plasmon resonance study. Analytical Chemistry 2001, 73, (24), 5796-5804.
24. Baty, A. M.; Leavitt, P. K.; Siedlecki, C. A.; Tyler, B. J.; Suci, P. A.; Marchant, R. E.; Geesey, G. G., Adsorption of adhesive proteins from the marine mussel, Mytilus edulis, on polymer films in the hydrated state using angle dependent X-ray photoelectron spectroscopy and atomic force microscopy. Langmuir 1997, 13, (21), 5702-5710.
25. Hansen, D. C.; Corcoran, S. G.; Waite, J. H., Enzymatic tempering of a mussel adhesive protein film. Langmuir 1998, 14, (5), 1139-1147.
26. Sever, M. J.; Weisser, J. T.; Monahan, J.; Srinivasan, S.; Wilker, J. J., Metal-mediated cross-linking in the generation of a marine-mussel adhesive. Angewandte Chemie, International Edition 2004, 43, (4), 448-450.
27. Suci, P. A.; Geesey, G. G., Comparison of adsorption behavior of two Mytilus edulis foot proteins on three surfaces. Colloids and Surfaces, B: Biointerfaces 2001, 22, (2), 159-168.
28. Yu, M. E.; Deming, T. J., Synthetic poly-peptide mimics of marine adhesives. Macromolecules 1998, 31, (15), 4739-4745.
29. Waite, J. H., Adhesion a la moule. Integrative and Comparative Biology 2002, 42, (6), 1172-1180.
30. Anderson, K. E.; Waite, J. H., Biochemical characterization of a byssal protein from Dreissena bugensis (Andrusov). Biofouling 2002, 18, (1), 37-45.
31. Dalsin, J. L.; Messersmith, P. B., Surface modification for protein resistance using a biomimetic approach. Materials Research Society Symposium Proceedings 2003, 774, (Materials Inspired by Biology), 75-80.
32. Dalsin, J. L.; Tosatti, S.; Textor, M.; Messersmith, P. B., Cloud point PEGylation of titanium biomaterials using a biomimetic anchor. Polymer Preprints (American Chemical Society, Division of Polymer Chemistry) 2003, 44, (1), 167-168.
33. Ooka, A. A.; Garrell, R. L., Surface-enhanced Raman spectroscopy of DOPA-containing peptides related to adhesive protein of marine mussel, Mytilus edulis. Biopolymers 2000, 57, (2), 92-102.
34. Monahan, J.; Wilker, J. J., Cross-Linking the protein precursor of marine mussel adhesives: Bulk measurements and reagents for curing. Langmuir 2004, 20, (9), 3724-3729.
35. Beiderbeck, H.; Taraz, K.; Budzikiewicz, H.; Walsby, A. E., Anachelin, the siderophore of the cyanobacterium Anabaena cylindrica CCAP 1403/2A. Zeitschrift fur Naturforschung. C, Journal of biosciences 2000, 55, (9-10), 681-7.
36. Gademann, K.; Budzikiewicz, H., The peptide alkaloid Anachelin: NMR spectroscopic evidence for b-Turn formation in aqueous solution. Chimia 2004, 58, (4), 212-214.
37. Gademann, K., Mechanistic Studies on the Tyrosinase-Catalyzed Formation of the Anachelin Chromophore. ChemBioChem 2005, 6, 913-919.

The invention claimed is:

1. A compound capable of forming adlayers and having one of the general formulas (A) to (C) below:

wherein A designates at least one headgroup A, B designates an optionally present linker B, C designates a polymer C, D designates an optionally present terminus D and R designates an optionally present crosslinker R, and wherein
the headgroup A is a compound of the following formula wherein
X is independently from each other selected from an acidic group comprising OH, SH, phosphate, phosphonate, and $N^+R_2H$, wherein the R are independently from each other selected from H or $C_1$-$C_6$ alkyl,
Y is a group derived from a convenient coupling group comprising $NL^3$, or $N^+(L^3)_2$,
$Z^1$, $Z^3$, and $Z^4$ are C or $N^+$
$Z^2$, $Z^5$ and $Z^6$ are C-$L^1$ or $N^+$-L, wherein
$L^1$ is H or an electron withdrawing group, whereby in the case of $L^1$=$NR^1R^2R^{3+}$, each of $R^1$, $R^2$, $R^3$ may be selected from C1-C6 alkyl or C5 or C6 aryl,
L is $C_1$-$C_4$-alkyl,
$L^2$ and $L^3$ are independently selected from H or $C_1$-$C_6$ alkyl, or $L^2$ may form together with $L^1$ or L of $Z^6$ a heterocycle,
n is 0, or 1, or 2, or 3,
m is 0 or 1
with the proviso that at most one of $Z^1$ to $Z^6$ is $N^+$ and that in case that $Z^1$ is $N^+$, $L^2$ may additionally be an ester, an amide, or a heterocycle, the optional linker B refers to one of the general formulas I, II, III or IV below where m and n are independently from each other 0, 1, 2, 3, 4, or 5, A refers to the headgroup A described above, and C refers to the polymer C, said polymer C being either of the general formula I or II wherein X is a group which can be chemically coupled to either A or the optional linker B, Y is a polymer, or an alkyl chain, Z is a functional group suitable for coupling to a terminus D, and the optional terminus D is either an inert group or a reactive group, and the optional crosslinker R is any molecule capable of crosslinking, and wherein in the headgroup A, $L^1$ bound to $Z^6$ is $NR^1R^2R^{3+}$, or $NO_2$, or F or $C_xF_y$, whereby in the case of $L^1=NR^1R^2R^{3+}$, each of $R^1$, $R^2$, $R^3$ may independently from each other be selected from $C_1$-$C_6$ alkyl or $C_5$ or $C_6$ aryl.

2. The compound of claim 1, wherein each of $R^1$, $R^2$, $R^3$ may independently from each other be selected from methyl, ethyl, n-propyl or iso-propyl, or wherein one of $R^1$ or $R^2$ or $R^3$ and $L^2$ form together a 5-membered or 6-membered heterocycle.

3. The compound of claim 1, wherein the headgroup A either refers to I, or II or III, or IV wherein $R^1$, $R^2$, $L^2$, $L^3$ and n are as defined above, wherein $L^2$ may also be an ester or amide, but not $CO_2H$ and wherein the deprotonated group indicates the improved deprotonation characteristics of the groups of formula II, III and IV.

4. The compound of claim 1, wherein the terminus D is either an inert group selected from the group consisting of alkyl, aryl, allyl, alkenyl, alkinyl, or polyalkylsilyl group, or a fluorescent marker, a biologically active compound selected from the group consisting of proteins, peptide sequences, and sacharides, or any other biologically active compound, or mixtures thereof, or a reactive group, selected from the group consisting of vinylsulfone, maleimide, acrylate, azide, alkine group or mixtures thereof.

5. The compound of claim 1, wherein the crosslinker R is selected from the group consisting of catechol, styrene, acrylates, thioles, thiophene, pyrrole, and combinations thereof.

6. The compound of claim 1 comprising more than one headgroup A per polymer C.

7. The compound of claim 1 comprising a terminus D.

8. The compound of claim 1 comprising a linker B.

9. The compound of claim 1 comprising a crosslinker R.

10. The compound of claim 1 comprising a headgroup A, a polymer C, and a terminus D.

11. The compound of claim 1 comprising one headgroup A, a linker B, a polymer C, and a terminus D.

12. The compound of claim 1 comprising two or three headgroups A, a linker B, a polymer C, and a terminus D.

13. The compound of claim 1 having the formula wherein $R^1$ and $R^2$ are as defined above.

14. The compound of claim 1 having the formula mPEG 5000 wherein $R^1$ and $R^2$ are as defined above.

15. The compound of claim 1 having the formula mPEG 5000

16. The compound of claim 1 wherein $Z^1$ is $N^+$ and $L^2$ is selected from the group consisting of C1-C4 alkyl, amide, and ester.

17. The compound of claim 1 having the formula

18. A compound having a $pK_{a1}$ of at most 9.9, said compound being capable of forming adlayers and having one of the general formulas (A) to (C) below:

$$A\text{—}B\text{—}C\text{—}D \quad \text{or} \quad (A)$$

wherein A designates at least one headgroup A, B designates an optionally present linker B, C designates a polymer C, D designates an optionally present terminus D and R designates an optionally present crosslinker R, and wherein
the headgroup A is a compound of the following formula wherein
X is an acidic group and is independently from each other, X comprising OH, SH, phosphate, phosphonate, $N^+R_2H$, wherein both R independently from each other are selected from H or $C_1$-$C_6$ alkyl,
Y is a group comprising the polymer C and the optionally present linker B, the optionally present terminus D and the optionally present crosslinker R,
$Z^1$, $Z^3$, and $Z^4$ are C or $N^+$,
$Z^2$, $Z^5$ and $Z^6$ are C-$L^1$ or $N^+$-L, whereby
$L^1$ is H or an electron withdrawing group and L is a neutral group, and
wherein in the headgroup A, $L^1$ bound to $Z^6$ is $NR^1R^2R^{3+}$, or $NO_2$, or F or $C_xF_y$ whereby in the case of $L^1$=$NR^1R^2R^{3+}$, each of $R^1$, $R^2$, $R^3$ may independently from each other be selected from $C_1$-$C_6$ alkyl or $C_5$ or $C_6$ aryl.

19. The compound of claim 18, wherein said compound is a compound according to claim 1.

20. The compound of claim 18, wherein X are both OH.

21. The compound of claim 1, wherein X are both OH.

22. The compound of claim 1, wherein $L^1$ is $L^1$=$NR^1R^2R^{3+}$, each of $R^1$, $R^2$, $R^3$ may be selected from methyl, ethyl, n-propyl or iso-propyl.

23. The compound of claim 1, wherein $L^2$ forms together with $L^1$ or L of $Z^6$ a positively charged heterocycle.

24. The compound of claim 1, wherein Y is an alkyl chain comprising a ($CR_2$) chain with n being at least 3 and R being independently from each other H or F.

* * * * *

UNITED STATES PATENT AND TRADEMARK OFFICE
CERTIFICATE OF CORRECTION

PATENT NO.       : 8,568,872 B2                                            Page 1 of 1
APPLICATION NO.  : 12/064564
DATED            : October 29, 2013
INVENTOR(S)      : Textor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1498 days.

Signed and Sealed this
Fifteenth Day of September, 2015

Michelle K. Lee
*Director of the United States Patent and Trademark Office*